(12) United States Patent
Heckenberger et al.

(10) Patent No.: US 8,641,981 B2
(45) Date of Patent: Feb. 4, 2014

(54) DEVICE FOR THE DISINFECTION, STERILIZATION AND/OR MAINTENANCE OF MEDICAL IN PARTICULAR DENTAL, INSTRUMENTS

(75) Inventors: Hans Heckenberger, Assmannshardt (DE); Hans-Dieter Wiek, Hochdorf (DE); Herbert Lott, Bad Wurzach-Arnach (DE); Frank Saur, Ulm (DE); Johann Stempfle, Pfaffenhofen (DE)

(73) Assignee: Kaltenbach & Voigt GmbH, Biberach (DE)

( * ) Notice: Subject to any disclaimer, the term of this patent is extended or adjusted under 35 U.S.C. 154(b) by 0 days.

(21) Appl. No.: 13/257,730

(22) PCT Filed: Mar. 19, 2010

(86) PCT No.: PCT/EP2010/053604
§ 371 (c)(1),
(2), (4) Date: Nov. 14, 2011

(87) PCT Pub. No.: WO2010/106161
PCT Pub. Date: Sep. 23, 2010

(65) Prior Publication Data
US 2012/0058007 A1   Mar. 8, 2012

(30) Foreign Application Priority Data

Mar. 20, 2009 (DE) .......................... 10 2009 014 065
Feb. 17, 2010 (DE) .......................... 10 2010 002 030

(51) Int. Cl.
*A61L 9/00* (2006.01)
*B08B 5/04* (2006.01)
*B08B 9/00* (2006.01)

(52) U.S. Cl.
USPC ........... 422/295; 422/292; 422/294; 422/300; 433/82; 134/95.1; 134/57 R; 134/170; 134/186

(58) Field of Classification Search
USPC ........... 422/1, 3, 26, 28, 32, 40, 33, 105, 114, 422/116, 119, 292, 294–295, 300; 433/82; 134/6, 8, 21, 22.1, 95.1, 57 R, 170, 186
See application file for complete search history.

(56) References Cited

U.S. PATENT DOCUMENTS

| 3,597,934 A | 8/1971 | Andersen et al. |
| 4,049,162 A | 9/1977 | Yule |

(Continued)

FOREIGN PATENT DOCUMENTS

| DE | 4021790 A1 | 1/1992 |
| DE | 4127776 A1 | 2/1993 |

(Continued)

OTHER PUBLICATIONS

European English translation of the description section of DE 4127776 A1.*

(Continued)

*Primary Examiner* — Monzer R Chorbaji
(74) *Attorney, Agent, or Firm* — Marshall, Gerstein & Borun LLP

(57) ABSTRACT

A device for the disinfection, sterilization and/or maintenance of medical, in particular dental instruments. The device is optimized in various areas, facilitating the fully automatic, reliable and reproducible preparation of dental instruments.

2 Claims, 4 Drawing Sheets

(56) References Cited

U.S. PATENT DOCUMENTS

| | | | |
|---|---|---|---|
| 5,552,113 A * | 9/1996 | Jennings | 422/26 |
| 5,823,340 A | 10/1998 | Maihofer | |
| 5,906,802 A * | 5/1999 | Langford | 422/300 |
| 2004/0001783 A1 * | 1/2004 | Bowen | 422/292 |
| 2004/0050383 A1 | 3/2004 | Cox et al. | |
| 2004/0190883 A1 | 9/2004 | Kompara et al. | |
| 2005/0112040 A1 | 5/2005 | Hasegawa et al. | |
| 2005/0130473 A1 | 6/2005 | Annecke | |
| 2007/0031778 A1 * | 2/2007 | Helfenbein et al. | 433/82 |
| 2008/0086111 A1 | 4/2008 | Cowan et al. | |
| 2011/0206555 A1 | 8/2011 | Wiek et al. | |

FOREIGN PATENT DOCUMENTS

| | | | | |
|---|---|---|---|---|
| DE | 4127776 (A1) | * | 2/1993 | B01J 3/03 |
| DE | 9404372 U1 | | 6/1994 | |
| EP | 882457 A2 | | 12/1998 | |
| EP | 890337 A2 | | 1/1999 | |
| EP | 1121942 A2 | | 8/2001 | |
| EP | 1484069 A1 | | 12/2004 | |
| EP | 1543889 A1 | | 6/2005 | |
| EP | 1749502 A1 | | 2/2007 | |
| JP | 2002002626 A | | 1/2002 | |
| JP | 2004073528 A | | 3/2004 | |
| WO | WO-0059553 A1 | | 10/2000 | |
| WO | WO-2006135647 A2 | | 12/2006 | |
| WO | WO-2007008618 A2 | | 1/2007 | |
| WO | WO-2009129902 A1 | | 10/2009 | |

OTHER PUBLICATIONS

International Search Report for PCT/EP2010/053604 dated Nov. 12, 2010.
International Search Report for PCT/EP2010/053601 dated Jul. 19, 2010.
International Search Report for PCT/2010/053602 dated Jan. 17, 2011.
Prof. Dr.—Ing Klaus Strohmeier, "Komponenten des Anlagenbaus", p. 154a. (Dec. 1, 2002).
Prof. Dr.—Ing. Klaus Strohmeier, "Beanspruchungsgerechte Anlagensimulation", p. 42h (Dec. 1, 2002).
International Preliminary Report on Patentability for Application No. PCT/EP2010/053601, dated Sep. 20, 2011.
International Preliminary Report on Patentability for Application No. PCT/EP2010/053602, dated Sep. 20, 2011.
International Preliminary Report on Patentability for Application No. PCT/EP2010/053604, dated Sep. 20, 2011.
Written Opinion for Application No. PCT/EP2010/053601, dated Jul. 19, 2010.
Written Opinion for Application No. PCT/EP2010/053602, dated Mar. 10, 2011.
Written Opinion for Application No. PCT/EP2010/053604, dated Jan. 6, 2011.

* cited by examiner

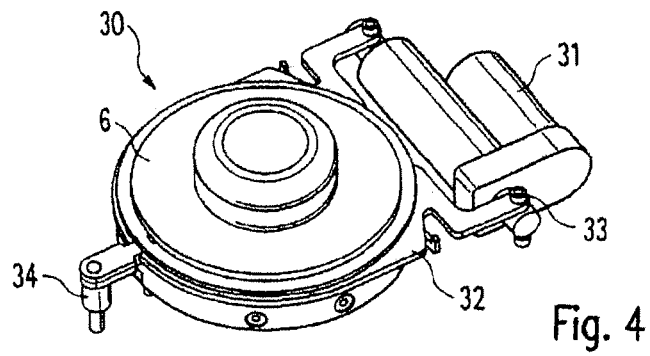
Fig. 4
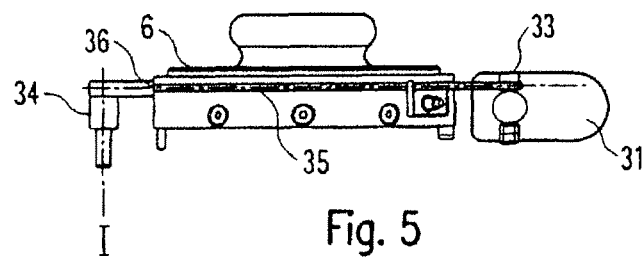
Fig. 5
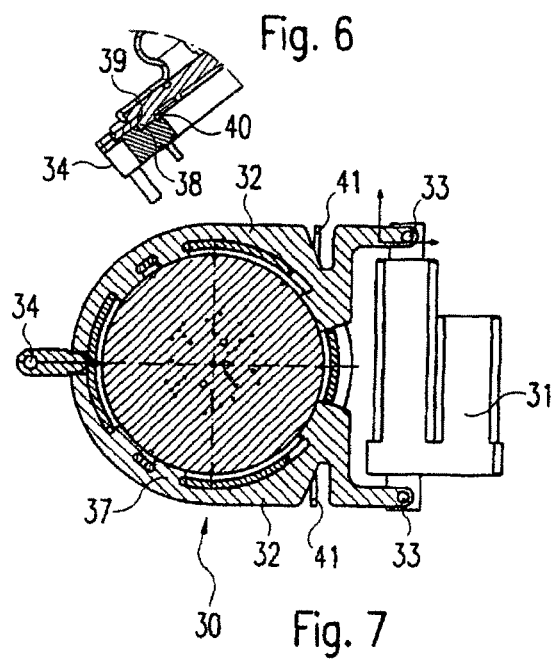
Fig. 6
Fig. 7

DEVICE FOR THE DISINFECTION, STERILIZATION AND/OR MAINTENANCE OF MEDICAL IN PARTICULAR DENTAL, INSTRUMENTS

BACKGROUND OF THE INVENTION

1. Field of the Invention

The present invention relates to a device provided for disinfecting, sterilizing and/or maintaining medical instruments. More particularly, the device should be used to prepare dental instruments.

2. Related Technology

Medical or dental handpieces are tubular parts that the medical practitioner grips as a handle sleeve during the treatment. A handpiece usually used in dental practice is a so-called drill handpiece, which carries a treatment tool, more particularly a drill, at its front end and the back end of which is coupled to a supply tube by means of a coupling. Feed lines for energy for driving the treatment instrument and fluid lines for treatment media, e.g. air and/or water, extend through the handpiece. A distinction is often made between so-called turbine handpieces, in which pressurized air is provided for feeding a turbine arranged in the front end region, and so-called motor handpieces, which have an electric motor as a drive unit.

In order to maintain the function of the handpieces, maintenance is required from time to time, particularly for the rotatably mounted drive elements. Furthermore, the ever more stringent hygienic requirements in dental practice lead to handpieces having to be prepared at regular time intervals. The successful preparation and maintenance of the appropriate requirements must be recorded in full by the dentist; this entails not insignificant personal and organizational effort.

Until now, dental handpieces were manually reprocessed by the instruments firstly being spray-disinfected after use on the patient and being externally washed. By contrast, in general the interior of the instruments was not cleaned. However, in the meantime cleaning and disinfection devices are commercially available, in which the instruments are prepared, before they are subjected to oil care. Machine preparation has significant advantages over manual maintenance of the instruments since only machine methods allow safe and reproducible cleaning and maintenance.

However, the devices known up until now can generally only be used for individual preparation steps, and so cleaning, maintenance and sterilization have to be carried out separately in each case. The totality of the devices required for this takes up a relatively large amount of space, with each device respectively requiring electric, pneumatic and fluidic connections. Accordingly, the implementation of a complete machine preparation of dental instruments by means of individual devices is very awkward and connected with great expense.

A further disadvantage consists of the fact that the individual devices generally are not interconnected, which is why there cannot be data interchange between the devices. This in turn leads to more overheads for the operating staff because it is not possible to create a continuous automatic documentation of the instrument preparation. Furthermore, the instruments have to be conveyed manually from device to device in intermediate steps, which entails intensive employment of staff and requires much time.

SUMMARY OF THE INVENTION

The present invention is therefore based on the object of specifying a novel device for disinfecting, sterilizing and/or maintaining, or generally for preparing, medical, more particularly dental, instruments, which device avoids the aforementioned disadvantages.

According to the present invention, a device is accordingly specified for preparing dental instruments in particular, which device allows intensive (internal and external) cleaning of the instruments using cleaning products and/or rinse aids at different temperatures. According to the invention, this is a fully automatic device that only requires servicing by staff after relatively long time intervals. This servicing is primarily restricted to refilling the consumables, i.e. the cleaning and maintenance products. By contrast, the instruments themselves are prepared without intervention by the staff, which can be traced back to a fully automatic process, including the option of creating documentation. In order to achieve this goal, a maintenance device is proposed that was optimized in a number of aspects, as described in more detail below.

Here, a first aspect of the present invention relates to the design of the device, more precisely the rinsing chamber, in which the dental instruments to be prepared are arranged. It is necessary to design the rinsing chamber as a pressure/vacuum container, which can be sealed in a simple and secure fashion, because there are different pressures and temperatures in the rinsing chamber during the cleaning and maintenance of the instruments.

In order to achieve this object, a device for disinfecting, sterilizing and/or maintaining medical, more particularly dental, instruments is proposed as per a first aspect of the present invention, which device has a rinsing chamber, a cover for closing the rinsing chamber, and a sealing mechanism for providing a seal between the cover and the rinsing chamber during operation. According to the invention, provision is made in this case for the sealing mechanism to have one or more clamps, which are mounted in a pivotable fashion about an axis aligned perpendicular to the plane of the cover in order to provide a seal between the cover and the container.

As will be explained in more detail below, this provides a sealing mechanism for the cover that is very simple to operate and at the same time ensures very secure sealing of the rinsing chamber. Specific measures can eliminate misoperation of the device and can accordingly increase operational safety.

In the process, provision is preferably made for the sealing mechanism to have two clamps that have a common pivot axis. In the process, the two clamps can then, at an end opposing the pivot axis, each be mounted on a drive for pivoting the clamps. This drive is a lift cylinder, more particularly an electric cylinder, which is preferably integrated into a handle for opening and closing the cover. The clamps can each have a bevel, which bevels interact with a bevel provided on the cover so that as the sealing apparatus is closed the cover is pressed against the chamber. In order to achieve a secure sealing, the clamps can have clamping projections for this purpose that grip through recesses provided in an end region of the container facing the cover.

A second aspect of the present invention relates to the problem of supplying the different media to the rinsing or process chamber. It is necessary to be able to convey these media, individually in each case, to the chamber because these are a plurality of different media, which are used in different phases of the instrument preparation. Feed pumps have up to now been used for this purpose, with each medium being assigned its own pump. It is obvious that this type of media conveyance is connected to great material expenditure and, accordingly, to high costs as well.

According to a second aspect of the present invention, in order to avoid the great expenditure, a device for disinfecting, sterilizing and/or maintaining medical, more particularly dental, instruments is accordingly proposed, which device has a rinsing chamber and a media supply system designed to route at least one medium, more particularly a cleaning or maintenance product, into the rinsing chamber. According to the invention, the device in this case furthermore has means for generating a defined negative pressure in the rinsing chamber, with the medium being supplied by opening a connection line from a storage container for the medium to the rinsing chamber.

Here, the connection line can in particular have a controllable valve, with the connection line being opened in a time-controlled and/or pressure-controlled fashion. Here, the negative pressure in the rinsing chamber in particular lies in the region of approximately 500 mbar.

According to this second aspect of the present invention, a method is also proposed for supplying a medium, more particularly a cleaning or maintenance product, into the rinsing chamber of a device for disinfecting, sterilizing and/or maintaining medical, more particularly dental, instruments, wherein according to the invention a defined negative pressure is generated in the rinsing chamber for supplying the medium and a connection line from a storage container to the rinsing chamber is subsequently opened.

The solution according to the invention affords the possibility of dispensing with respectively individual feed pumps for the different media. All that is required is a single component that is able to generate a vacuum within the process chamber or rinsing chamber. The complexity in conveying individual media is thus significantly reduced.

Finally, a third aspect of the present invention also relates to the metering of the amount of media supplied during the preparation of the dental instruments. It goes without saying that the amount of maintenance or cleaning products in this case also depends on the number of instruments to be prepared. This number can certainly vary, which is why information in respect of the number of instruments to be prepared should be provided to the device. Here, the third aspect of the present invention allows automatic identification of the instruments that should in fact be cleaned.

According to the invention, a device is proposed to this end for disinfecting, sterilizing and/or maintaining medical, more particularly dental, instruments, which device has a rinsing chamber, holders that are situated in the rinsing chamber, serve for holding the instruments and each have a coupling valve, a pressurized-air and cleaning product feeding system, and means for identifying the occupancy of the couplings by instruments. According to the invention, the means for identifying the occupancy of the holders by instruments are designed to determine the occupancy of the holder by an instrument on the basis of the subsequent pressure drop in the chamber after the generation of a positive pressure in the rinsing chamber and the opening of the coupling valve of a holder. In the process, the means can furthermore be designed to establish, in succession, the occupancy of every single holder by an instrument.

As per this third aspect of the invention, a method is furthermore proposed for identifying the occupancy of instrument holders in a device for disinfecting, sterilizing and/or maintaining medical, more particularly dental, instruments, wherein the device has a rinsing chamber and holders, which are situated in the rinsing chamber and serve for holding the instruments, which holders each have a coupling valve. According to the invention, a positive pressure is generated in the rinsing chamber for identifying the occupancy of the holders by instruments. The coupling valve of a holder is subsequently opened and the occupancy of the holder by an instrument is determined on the basis of the subsequent pressure drop in the chamber.

As an alternative to the procedure described above, provision could also be made for identifying the occupancy of the holders by instruments with the aid of an inductive or capacitive measurement system. Here, the fact is utilized that the instruments to be prepared are generally metallic objects. If an inductive element or a capacitive element is situated in the vicinity of the holders, this element is influenced by the presence of an instrument. This effect can be evaluated in order to identify the occupancy of the couplings.

This third aspect of the invention correspondingly affords the possibility of identifying, in a simple and elegant fashion, whether an instrument holder is in actual fact occupied by an instrument to be cleaned. Correspondingly accurate and reliable metering of the various cleaning or maintenance products is ensured in this fashion.

In conclusion, a device is thus proposed that affords the possibility of preparing in particular dental instruments in a fully automatic, reliable and reproducible fashion.

BRIEF DESCRIPTION OF THE DRAWINGS

In the following text, the invention shall be explained in more detail on the basis of the attached drawing, in which:

FIGS. 4 to 7 show illustrations of a cover, which is arranged on the top side of the rinsing chamber and can be used to provide a seal with the rinsing chamber;

DETAILED DESCRIPTION

Figure 1:
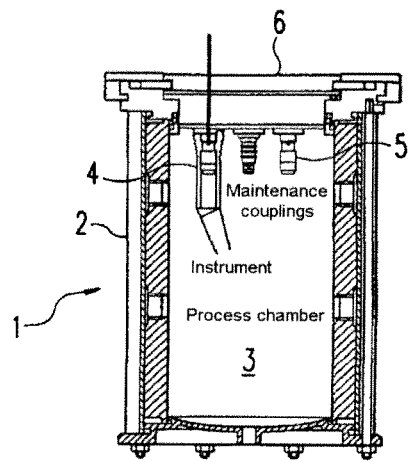
FIG. 1 shows a sectional illustration of a process or rinsing chamber of a device in accordance with the invention for disinfecting, sterilizing and/or maintaining dental instruments.

FIG. 1 first of all schematically shows the design of a device according to the invention for disinfecting, sterilizing and/or maintaining medical, more particularly dental, instruments, with the device in general being denoted by the reference sign 1 below. A central element of the maintenance device 1 according to the invention is a pressure container 2, which surrounds a process or rinsing chamber 3. During the process, the instruments 4 to be cleaned or maintained are arranged in this rinsing chamber 3. Here, the instruments 4 are arranged with the aid of an instrument holder, on which a plurality of plug-in points or couplings 5 are arranged. Provision is preferably made for various couplings 5, so that it is possible to prepare instruments 4 having coupling systems from different manufacturers. In the present case, the cover 6 of the process chamber 3 serves as instrument holder, which will be described in more detail below. This cover 6 ensures the fluidic coupling to a supply system of the instruments 4 to be cleaned. It is clamped onto the rim or flange of the pressure container 2 by a sealing unit (described in more detail below) and sealed with respect to this container. A cleaning and/or maintenance product can then be applied to the individual instruments 4 and the channels thereof, individually or in combination, via connecting tubes integrated into the cover 6.

Before individual components or elements of the device according to the invention are now discussed in more detail, the process when cleaning and/or maintaining the instruments 4 shall first of all be described in general terms. Here, the pressure seal of the process chamber 3 is checked before the preparation is started. In the process, it is ensured that the cover 6 has been applied correctly and sealed to the pressure container 2. A check is also carried out as to whether the fluid lines between the cover 6 and the lines running in the flange of the pressure container 2 are correctly connected.

In order to supply the device 1 with water, tap water is preferably filtered by means of an osmosis installation with or without downstream mixed-bed ion exchanger, with the dissolved salts being removed. The water with a quality of <15 μS/cm is routed into a device-side storage container, where the filling level is monitored via a level switch, which is embodied as a float switch, and the quality is monitored via a conductance sensor. The inlet into the storage container is embodied with a so-called cascade for reasons of hygiene.

When the instruments are prepared with the aid of the device according to the invention, the following steps are then carried out in succession:

a) Cleaning

The water is first of all routed from the above-described storage container into the process chamber 3, wherein this can be brought about via a pump or—as described below—by suction via a vacuum. The water is heated to approximately 45° C. in the process chamber 3 with the aid of heating elements. In the process, care is taken that the temperature is not above 45° C. in order to prevent proteins from coagulating. The water is furthermore circulated with the aid of a pump and directed onto the external surfaces of the instruments 4 via spray nozzles, which are attached on the lateral surface of the pressure container 2 or in a central dome, in order to clean the instruments. In the process, the cleaning water can be routed through the instruments 4 and/or the spray channels of the instruments 4 and/or through the spray nozzles of the process chamber 3 for external cleaning.

The washing medium can be heated during the circulation, and so the surfaces to be cleaned are at first cleaned by a cold washing medium. The cleaning product can in this case be added to the process chamber 3 in the form of a powder or in tablet form, or it can be metered in from an appropriate storage container. The various options for metering the cleaning product are described below. The washing medium can in this case consist of surfactants or phosphates and have a pH-value of greater than 10. In order to complete the washing process, the water is let out of the pressure container 2.

b) Rinsing—Neutralization

In a subsequent step, the water is then routed into the process chamber 3 from the storage container and now it is heated to approximately 45° C. to 60° C. Rinse aid or neutralizer is added in a metered fashion from a further storage container during the circulation of the water. Alternatively, as a result of the higher temperature compared to step a), a second component of a cleaning tablet can now also be dissolved. The liquid is, once again in a parallel or time-offset fashion, or in an interval operation, routed through the instruments 4 and the spray channels or directed on the external surfaces of the instruments 4 via the spray nozzles. Phosphoric acid ester with a pH-value of between 3 and 5 in particular is used as rinse aid or neutralizer.

The liquid can be let out of the pressure container again and into the drain, or it remains in the container in order to take up excess maintenance product emerging from the instruments 4 in the subsequent maintenance process or to rinse the oily external instrument surface briefly with warm liquid. In this case, the liquid is only let out after the maintenance process, with it possibly being helpful to apply pressurized air to the instruments 4 in order to prevent spray water from penetrating into the interior of the instruments 4.

c) Maintenance

In a third step, maintenance product from a maintenance product storage container is routed into the interior of the instrument, so that the gears and bearing surfaces are lubricated. Here, the maintenance product can be injected in a pressurized-air jet in liquid form as oil or from a gas cylinder. The oil can also be foamed via the foaming agent contained in the gas cylinder and the interior of the instrument can be filled with this oil/air foam. In this case, the air bubbles collapse relatively quickly, and so the oil forms a uniform thin oil film in the entire interior of the instruments. Biodegradable fatty acid-ester oil/white oil mixtures are used as lubricants.

d) Rinsing Off

After the maintenance process described above, the external sides of the instruments can be rinsed off with the rinse-aid liquid still located in the container. As an alternative to this, fresh water from the storage container is routed into the process chamber 3 via a pump and directed on the external surfaces of the instruments via the spray nozzles.

e) Sterilization—Pre-Vacuum

Fresh water from the storage container is fed into the process chamber 3 for the purpose of sterilizing the instruments. For ventilation purposes, a vacuum apparatus is connected in the process chamber 3, with the pressure within the process chamber 3 being monitored or registered.

The air is suctioned out of the process chamber 3 with the aid of the vacuum apparatus. The vacuum is reduced to atmospheric pressure by heating the water via heating elements. The process chamber 3 is then filled with water vapor, wherein, depending on the sterilization program, this process can be repeated a number of times.

The evaporated water volume can be refilled in every vacuum cycle, wherein, as an alternative to this, the complete amount of water required for generating the steam can also be introduced into the process chamber 3 directly at the start of the sterilization cycle.

As an alternative to generating steam by heating elements situated in the process chamber 3, water vapor can also be fed in from a steam pressure chamber, situated outside of the process chamber 3, for equalizing the pressure during the ventilation and for the sterilization.

f) Drying and Cooling

Once the sterilization is complete, the instruments 4 are dried by condensing the water vapor situated in the process chamber 3. This is achieved by virtue of the fact that the container wall or elements situated in the container are cooled, for example by routing water through them, which water was taken from the storage container. Here, the water can be fed continuously or during intervals. The water is led away after the cooling process is complete. The cover 6 can be opened because the temperature within the chamber 3 has now dropped below 50° C. This completes the preparation cycle for the instruments 4.

What emerges from the description above is that the device 1 according to the invention allows a fully automatic preparation of dental instruments. The operating staff no longer needs to take action and so this is a very convenient system. Individual details of this device shall be described in more detail below.

Figure 2:
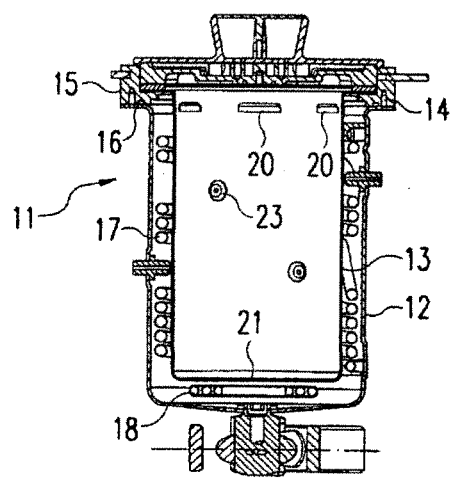
FIGS. 2 and 3 show a possible design of a rinsing chamber of the instrument in FIG. 1.
Figure 3:
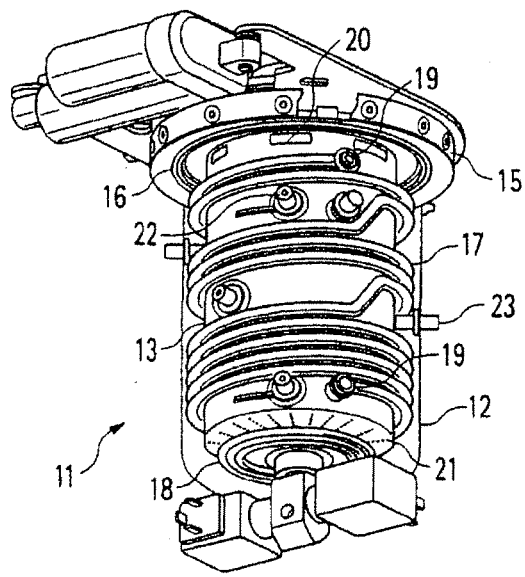

Here, FIGS. 2 and 3 shall first of all be used to explain an advantageous embodiment of a process chamber or a rinsing container. Here, the container was optimized in order to reduce the cycle times for the heating and cooling phases during the preparation steps of the instruments.

The process or rinsing chamber, in general denoted by the reference sign 11, is to this end made from a deep-drawn external container 12, which is embodied as a pressure container, and a deep-drawn thin-walled internal container 13. Alternatively, the two containers 12 and 13 can also be embodied as a welded construction from a plurality of parts. Here, the external container 12 is screwed to the container flange 15 via screw connections 14. A seal 16 in the form of an encircling sealing ring is formed between external container 12 and container flange 15.

The internal container 13 is suspended in the container flange 15 and can simply be removed upward for cleaning the rinsing chamber or replacing the heater. In the process, the position of the internal container 13 is fixed by pins embodied on the container flange 15 and corresponding recesses on the internal container 13. This ensures that, in respect of the openings for the cleaning nozzles for cleaning the instruments (not illustrated), the internal container 13 is positioned correctly.

A cooling coil 17 and a heating coil 18 are situated in the interspace between external container 12 and internal container 13. Since the internal container 13 is not sealed with respect to the external container 12 (this will be explained in more detail below), the entire area of the cooling coil 17 and the heating coil 18 is situated within the rinsing chamber, which ensures optimum heat transfer or temperature coupling. In the illustrated exemplary embodiment, the surface of the cooling coil 17 is approximately 2.5 times the size of the cylindrical external lateral surface. Thus, a very large surface area is available for heat transmission. The cooling coil 17 is screwed to the external container 12 by means of soldered-on or welded-on adapters 19. Welding or soldering on the external container 12, as would be required in the case of a cooling coil situated on the outside, is not required in this solution. The heating coil 18, which is arranged on the underside of the internal container 13 in the illustrated exemplary embodiment, could alternatively also be applied internally or externally to the base as a sheet heating element.

In order to achieve effective steam circulation between the external container 12, more precisely between the interspace between the internal and external container, and the internal region of the internal container 13, apertures or passage openings 20 are provided in the upper region of the internal container 13. Further such apertures are situated in the vicinity of the cleaning nozzles and on the base. This base perforation 21 simultaneously acts as a sieve in order to prevent small parts from entering the outflow of the container.

Furthermore, temperature sensors 22 are arranged on the external surface of the internal container 13. These are embodied in angled form and protected from mechanical damage as a result of their arrangement.

The cleaning nozzles 23 are screwed to the external container 22 via a seal and spray the instruments through a corresponding opening on the internal container 13. The attachment regions of the various screw-in points in each case are stamped planar surfaces and can easily be sealed with respect to the respective component via e.g. O-rings, flat gaskets, etc. The heating coil 18 on the container base has a smaller external diameter than the internal diameter of the cooling coil 17 and can accordingly, if required, be removed or uninstalled without disassembling the cooling coil 17.

It goes without saying that the process chamber could also have a different design; for example, it could have a double wall, with the cavity between the walls then being used for conducting a coolant.

The steps described above can clearly only be carried out in an orderly fashion when preparing the instruments if the process chamber 3 is closed in a pressure-tight/vacuum-tight fashion. To this end, provision is made for a special cover with a sealing mechanism, which is illustrated in FIGS. 4 to 7 and shall be explained in more detail below.

Here the sealing mechanism 30 first of all has a lift cylinder 31, which is preferably embodied as an electric cylinder and has internal or external limit switches. Two arc-shaped sealing clamps 32 are attached to the lift cylinder 31 via hinges 33, with the clamps 32 being arranged on a bearing pin 34 on their opposite end. This bearing pin 34 defines a pivot or rotation axis I, aligned perpendicular to the plane of the cover 6, about which the two clamps 32 can be pivoted.

Here, both clamps 32 are mounted in a groove 35 in the container flange 36. When the clamps 32 are closed, clamping projections or claws 37 of the clamps 32 project through the container flange 36 and, via a bevel 38, press the container cover 6 onto a seal 40, which is situated on an end face and can for example be embodied as an encircling O-ring, via an encircling or partial groove 39. The groove 39 of the container cover 6 in this case has the same bevel as the claws 37 of the sealing clamps 32, so that interaction between the two elements is ensured.

If an electric cylinder is used as lift cylinder 31, the cover 6 is securely closed because the clamps 32 cannot open even in the case of a power failure as a result of the self-locking properties of the preferably utilized linear threaded shaft. The claws 37 of the clamps 32 and the cover groove 39 can also have a steeper bevel if the cover is not resting on the container seal 40 at the beginning of the closing process and if a relatively large linear movement is required for closing.

The two clamps 32 are preferably designed in such a way that one of the two clamps 32, which has a lower coefficient of friction, pivots up to one of the two stops 41 while the container is being opened. Only then does the second clamp 32 open. Here, the final positions of the clamps 32 in the opened and closed state can be detected by external limit switches or else by internal limit switches in the electric cylinder 31, or by appropriate combinations thereof.

In order to prevent damage resulting from a container cover 6 that has not been applied properly, if an electric cylinder 31 is used, it can be equipped with a current limiter. In order to ensure further that the cover 6 was properly applied, a negative pressure can briefly be generated in the container and be detected by a pressure sensor. The closing process can only take place once the negative pressure has reached a specific threshold, which can only be attained if the cover 6 was applied properly.

This is a simple, self-centering system in which attaching the sealing clamps 32 on the lift cylinder 31 at the same time assembles the whole system. Furthermore, an expedient, direct force flow is obtained from the cover 6 to the container flange via the clamps 32. When the cover 6 is locked, it is simultaneously pressed against the seal, and so there is secure sealing in the case of both negative and positive pressure. Furthermore, as a result of the end-faced sealing of the container, pressure that may be present is reduced immediately when opening the cover. As a result, the cover 6 cannot be accelerated upward and so this accordingly cannot lead to the operator being endangered.

It can be gathered from the procedural steps described above that different chemical substances are used for cleaning, maintenance and disinfection when the instruments are prepared. The substances are offered and utilized in different states (solid, powdery or liquid) and packaging (spray cans, liquid-dispenser bottles or tablets). Here, the different products are usually labeled by appropriate imprints on the packaging or the vessel.

In addition to storage containers in the form of spray cans, the device according to the invention also uses containers that provide, in a liquid form, media to be supplied. In particular, in the process described at the outset, water, purified water, liquid cleaner and rinse aid are added. In order to convey these media into the process chambers, a separate feed pump was required in the past for each medium. However, this type of media conveyance results in great complexity in materials and high costs.

Figure 8:
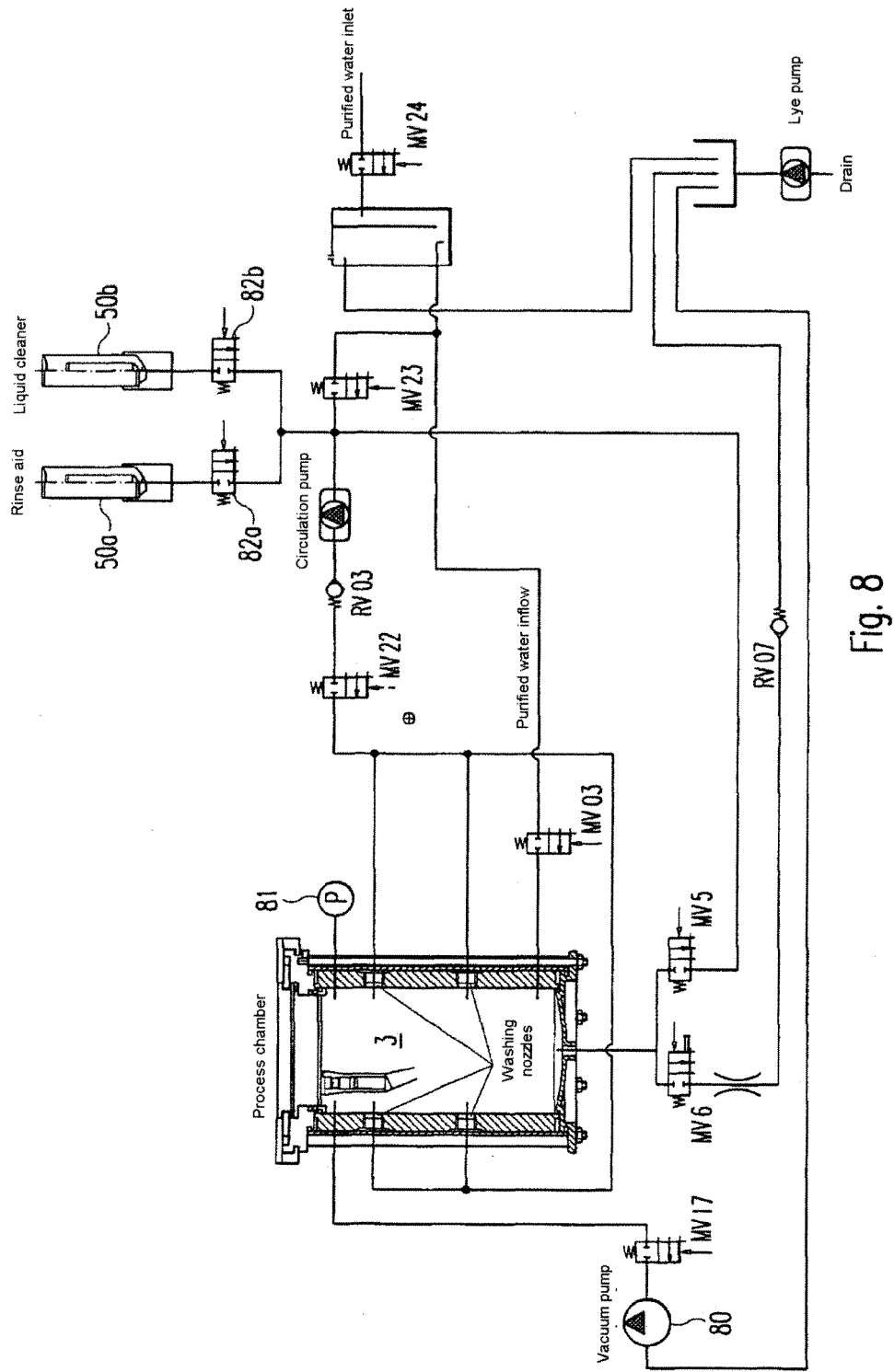
FIG. 8 shows the design of the system for removing media from storage containers by generating negative pressure in the rinsing chamber.

FIG. 8 now shows a solution of this problem that is based on generating a vacuum within the process chamber 3. To this end, use can be made of the vacuum pump 80, which is in any case required to carry out the various cleaning and maintenance steps. This pump 80 now generates a negative pressure within the process chamber of preferably approximately 500 mbar, wherein this pressure should be as accurate as possible in order to ensure precise metering of the media to be supplied. The pressure sensor 81, which is likewise usually already present, is used to monitor the vacuum within the process chamber 3.

If a specific medium should now be supplied, the valve 82a or 82b belonging to the associated storage container 50a, 50b is opened for a fixed period of time, determined experimentally in advance, so that the associated medium is sucked into the process chamber 3 as a result of the negative pressure. Accordingly, the desired medium can be conveyed into the process chamber 3 by opening the associated valve.

The conveyed medium can now for example be metered by virtue of the fact that the feed valve is opened for a predefined period of time. Accordingly, in this time-controlled variant, it must be established in advance what amount of media is conveyed into the chamber 3 over what period of time when the defined negative pressure is applied.

A pressure-controlled variant would alternatively also be possible. Here, after introducing the medium to be metered into the process chamber 3, the associated valve is opened until a second, lower negative pressure is obtained in the process chamber.

The medium to be metered flows in more rapidly at higher negative pressures, and slows down at lower negative pressures. It was found that a negative pressure of approximately 500 mbar leads to a very good compromise because this allows both rapid supplying or filling, and also high accuracy during the metering.

As a result of the solution according to the invention, in which the media are conveyed by the vacuum applied to the process chamber 3, the use of separate feed pumps can be dispensed with. The only media supplied to the process chamber are those whose feed valve to the process chamber is open when a vacuum is applied. Accordingly, the solution is significantly more cost-effective than previously known embodiments, with rapid but precise metering of the media being nevertheless obtained.

The idea of the invention described below also deals with the supplying or metering of the media used during the process. What now needs to be ensured in the process is that the amount of the medium supplied in each case is matched to the number of instruments to be prepared. The amount of media should accordingly be adapted depending on the number of occupied holders or maintenance couplings; this is why it is necessary to identify or set how many instruments are actually present within the process chamber.

The prior art has previously disclosed identifying the occupancy by way of various types of switches, via which the associated valves were then actuated. By contrast, in the case of a closed chamber, as is preferably the case in the present device, a corresponding identification of the instruments is more difficult. EP 1 749 502 A has furthermore disclosed a solution in which pressure is applied to the associated instrument feed lines; however, this solution required a plurality of pressure sensors.

Figure 9:
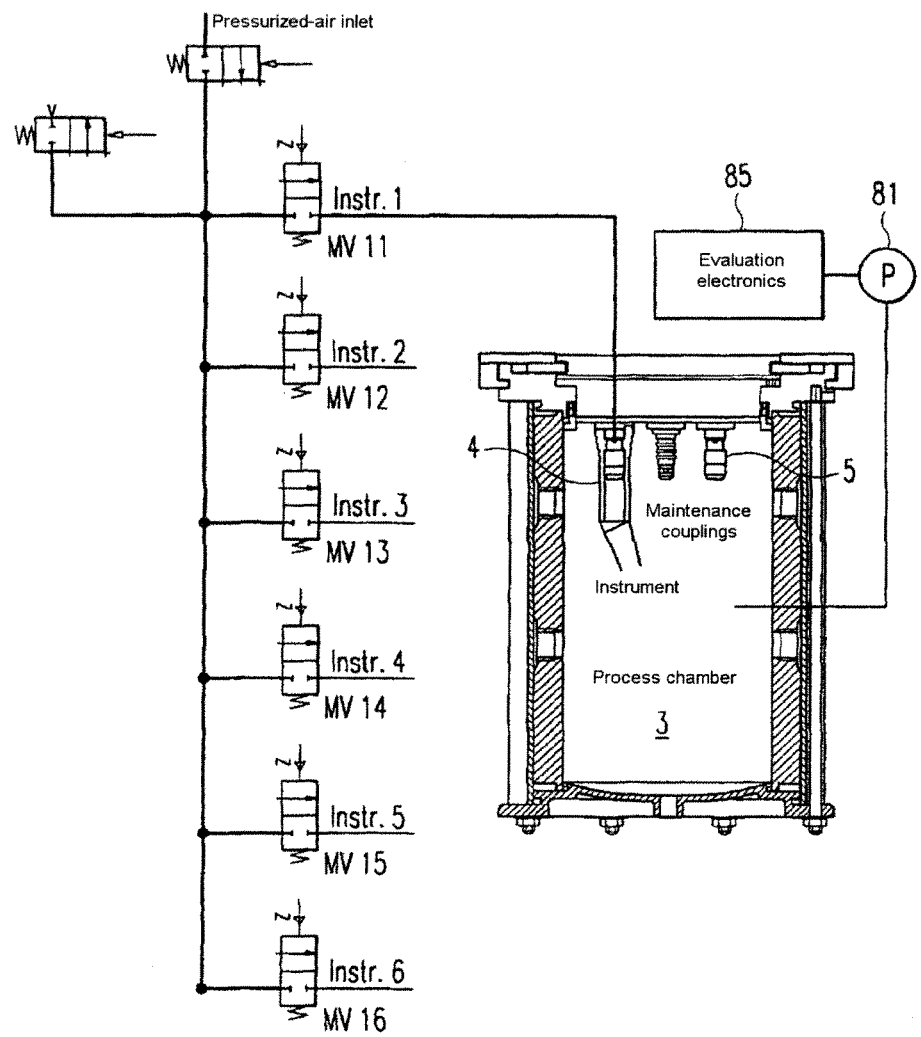
FIG. 9 shows the procedure for automatically identifying the occupancy of holders of the device by instruments to be prepared.

A simpler solution compared to this is illustrated in FIG. 9, which solution is based on the idea of using the pressure sensor 81, which is arranged within the process chamber 3 and is needed in any case for the sterilization procedure, for identifying occupancy.

In the solution according to the invention, a positive pressure is generated in the process chamber 3, and the coupling valve MV11-MV16 to be examined is subsequently opened. The valve MV11-MV16 then ventilates atmospherically, wherein the drop in pressure over a predetermined period of time setting in the process chamber 3 can be used to determine whether or not the addressed coupling 5 is occupied by an instrument 4. If there is a small drop in pressure, this means that the coupling 5 is occupied. By contrast, a large drop in pressure allows the deduction that the coupling 5 is not occupied. The couplings 5 can then in this fashion be queried in succession.

The procedure is illustrated schematically in FIG. 9, wherein pressurized air is firstly routed into the process chamber 3 via the valves MV10 and MV11 in order to generate a positive pressure of, for example, 0.5 to 2 bar, typically 1 bar. Subsequently, air is released from the process chamber 3 for a defined time between 1 and 10 seconds, e.g. 2 seconds, via the valves MV11 and MV31 and the pressure drop in the process chamber or the gradient of the pressure drop is established. The values of unoccupied couplings are stored in evaluation electronics 85, and so the created pressure difference can, via the evaluation electronics 85, be used to determine whether or not the appropriate coupling 5 is equipped with an instrument 4. This process is then repeated until all couplings 5 were queried.

It can be seen immediately that a single pressure sensor is sufficient to carry out the identification of the coupling occupancy according to the invention, which is why the method can be implemented in a very simple and cost-effective fashion. A further advantage consists of the fact that some dental instruments are, for reasons of hygiene, equipped with a system, e.g. a valve, that prevents back-suction of spray water into the instrument and the tube line during use. If pressure is applied from the side of the collet chuck, as envisaged according to the invention, this check valve closes and leads to a significant reduction in the pressure drop within the process chamber 3. Accordingly, the occupancy of the couplings with such instruments can be reliably identified. In contrast to this, in the solution according to the aforementioned EP 1 749 502 A, the pressure is applied from the coupling side, which leads to the check valve merely serving as a flow impediment, and so identifying the occupancy of the coupling is significantly more difficult in this case.

As an alternative to the procedure described above, it would also be feasible to establish the presence of the instruments with the aid of a capacitive or inductive measurement system. By way of example, a coil could be arranged in the vicinity of the couplings. If an instrument, which is a metallic object, is now in the vicinity of the coil, this results in an influence on the inductance of the coil. This inductance can be measured, as a result of which the occupancy of the coupling can be determined. The electronics for evaluating or establishing the presence of the instruments can advantageously be arranged on the means for distributing the media. The upshot of this is that only one identification system is required.

In one development, provision can furthermore be made for the system to adjust itself, for example by firstly establishing the inductance values in a state in which the couplings are unoccupied or a dummy instrument is arranged thereon.

It goes without saying that, as an alternative to the above-described inductive measurement, use can also be made of a capacitive element, the coupling of which to the instrument to be prepared in turn entails an influence on the capacitance.

Overall, accordingly, a concept is proposed according to the present invention for a device for disinfecting, sterilizing and/or maintaining medical, more particularly dental, instruments, which device was optimized in respect of a number of details in order to allow a fully automatic, reliable and reproducible preparation of dental instruments.

The invention claimed is:

1. A method for identifying the occupancy of instrument holders in a device for disinfecting, sterilizing and/or maintaining medical instruments, wherein the device has a rinsing chamber and holders situated in the rinsing chamber for holding the instruments, each holder having a coupling valve or being coupled to a valve, the method comprising:
   generating a positive pressure in the rinsing chamber for identifying the occupancy of the holders by instruments,
   opening the valve of a holder,
   measuring a drop in pressure in the rinsing chamber over a predetermined period of time, and
   determining the occupancy of the holder by an instrument on the basis of the measured pressure drop in the chamber.

2. The method as claimed in claim 1, comprising establishing the occupancy of every single holder by an instrument in succession.

\* \* \* \* \*